United States Patent
Zou et al.

(10) Patent No.: US 10,136,868 B2
(45) Date of Patent: Nov. 27, 2018

(54) FAST DUAL ENERGY FOR GENERAL RADIOGRAPHY

(71) Applicants: Yun Zou, Niskayuna, NY (US); John Michael Sabol, Waukesha, WI (US); Brian David Yanoff, Niskayuna, NY (US); Hao Lai, Niskayuna, NY (US); Biju Jacob, Niskayuna, NY (US); Katelyn Rose Nye, Waukesha, WI (US); Feng Chen, Niskayuna, NY (US)

(72) Inventors: Yun Zou, Niskayuna, NY (US); John Michael Sabol, Waukesha, WI (US); Brian David Yanoff, Niskayuna, NY (US); Hao Lai, Niskayuna, NY (US); Biju Jacob, Niskayuna, NY (US); Katelyn Rose Nye, Waukesha, WI (US); Feng Chen, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 331 days.

(21) Appl. No.: 14/844,695

(22) Filed: Sep. 3, 2015

(65) Prior Publication Data

US 2017/0065240 A1   Mar. 9, 2017

(51) Int. Cl.
*A61B 6/00* (2006.01)
*H01L 27/146* (2006.01)
*G01N 23/087* (2018.01)

(52) U.S. Cl.
CPC .............. *A61B 6/482* (2013.01); *A61B 6/405* (2013.01); *A61B 6/4208* (2013.01);
(Continued)

(58) Field of Classification Search
CPC ..................................................... A61B 6/482
See application file for complete search history.

(56) References Cited

U.S. PATENT DOCUMENTS 6,343,111 B1   1/2002   Avinash et al.
7,742,573 B2   6/2010   Caiafa et al.
(Continued)

FOREIGN PATENT DOCUMENTS

EP   1 216 661 A2   6/2002
EP   2 567 659 A1   3/2013
(Continued)

OTHER PUBLICATIONS

Kuhlman et al., "Dual-Energy Subtraction Chest Radiography: What to Look for beyond Calcified Nodules1", Radio Graphics, vol. No. 26, Issue No. 01, pp. 79-92, 2006.
(Continued)

*Primary Examiner* — Thomas R Artman
(74) *Attorney, Agent, or Firm* — GE Global Patent Operation; Pabitra K. Chakrabarti

(57) ABSTRACT

Some embodiments are associated with an X-ray source configured to generate X-rays directed toward an object, wherein the X-ray source is to: (i) generate a first energy X-ray pulse, (ii) switch to generate a second energy X-ray pulse, and (iii) switch back to generate another first energy X-ray pulse. A detector may be associated with multiple image pixels, and the detector includes, for each pixel: an X-ray sensitive element to receive X-rays; a first storage element and associated switch to capture information associated with the first energy X-ray pulses; and a second storage element and associated switch to capture information associated with the second energy X-ray pulse. A controller may synchronize the X-ray source and detector.

16 Claims, 13 Drawing Sheets

Figure 1:
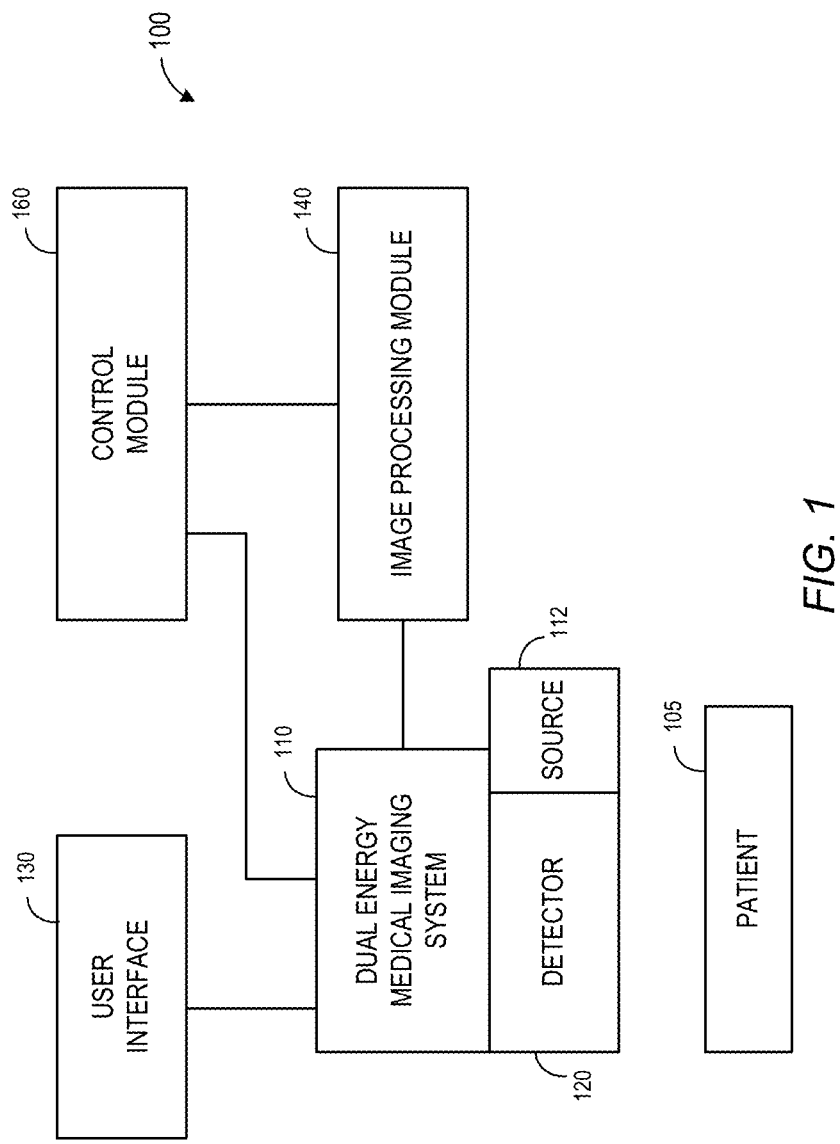

(52) U.S. Cl.
CPC ............ *A61B 6/4233* (2013.01); *A61B 6/542* (2013.01); *G01N 23/087* (2013.01); *H01L 27/14641* (2013.01); *H01L 27/14658* (2013.01)

(56) References Cited

U.S. PATENT DOCUMENTS

| | | | |
|---|---|---|---|
| 7,834,321 | B2 | 11/2010 | Yorkston et al. |
| 7,844,030 | B2 | 11/2010 | Wilson et al. |
| 8,027,433 | B2 | 9/2011 | Zou et al. |
| 8,165,264 | B2 | 4/2012 | Zou |
| 8,189,741 | B2 | 5/2012 | Ernest et al. |
| 8,320,521 | B2 | 11/2012 | Zou et al. |
| 8,396,185 | B2 | 3/2013 | Zou et al. |
| 8,401,151 | B2 | 3/2013 | Frontera et al. |
| 8,546,765 | B2* | 10/2013 | Ruetten ............ G01T 1/24 250/370.09 |
| 8,761,340 | B2 | 6/2014 | Yorkston et al. |
| 9,121,954 | B2* | 9/2015 | Pietig ............ G01T 1/17 |
| 9,257,460 | B2* | 2/2016 | Kikuchi ............ H01L 27/146 |
| 9,362,326 | B2* | 6/2016 | Kikuchi ............ H01L 27/146 |
| 2003/0169850 | A1 | 9/2003 | Kump et al. |
| 2007/0104311 | A1 | 5/2007 | Possin et al. |
| 2008/0144764 | A1 | 6/2008 | Nishide et al. |
| 2008/0232549 | A1 | 9/2008 | Poorter |
| 2011/0108735 | A1* | 5/2011 | Ruetten ............ G01T 1/24 250/371 |
| 2011/0150175 | A1 | 6/2011 | Hsieh et al. |
| 2013/0003928 | A1* | 1/2013 | Pietig ............ G01T 1/17 378/62 |
| 2013/0170615 | A1 | 7/2013 | Wei et al. |
| 2013/0343519 | A1 | 12/2013 | Ma et al. |
| 2014/0054445 | A1* | 2/2014 | Kikuchi ............ H01L 27/146 250/208.1 |
| 2014/0205070 | A1 | 7/2014 | Caiafa |
| 2015/0207415 | A1 | 7/2015 | Caiafa et al. |
| 2015/0359502 | A1 | 12/2015 | Zou et al. |
| 2016/0079298 | A1* | 3/2016 | Kikuchi ............ H01L 27/146 250/208.1 |
| 2017/0065240 | A1* | 3/2017 | Zou ............ A61B 6/482 |

FOREIGN PATENT DOCUMENTS

| | | |
|---|---|---|
| EP | 2749904 A2 | 7/2014 |
| WO | 2008088477 A2 | 7/2008 |

OTHER PUBLICATIONS

Fossum., "Guest Editorial Special Issue on Solid-State Image Sensors", IEEE Transactions on Electron Devices, vol. No. 56, Issue No. 11, pp. 2376-2379, Nov. 2009.

Aran et al., "Applications of Dual-Energy CT in Emergency Radiology", American Journal of Roentgenology, vol. No. 202, pp. W314-W324, Apr. 2014.

European Search Report and Opinion issued in connection with corresponding EP Application No. 16185845.1 dated Feb. 15, 2017.

* cited by examiner

FAST DUAL ENERGY FOR GENERAL RADIOGRAPHY

BACKGROUND

The invention relates to general radiography and, more particularly, to methods and systems providing fast Dual Energy ("DE") radiography for medical imaging and similar applications.

Generally, an X-ray generated by an X-ray tube may pass through a patient and then be detected by an x-ray detector. Detected X-ray levels may then be used to generate an image of the patient. To improve the quality of the image, two exposures of X-rays may be utilized, each at a different energy level. Such an approach is referred to as "dual energy" radiography.

One objective of dual energy radiography is to obtain images that enhance contrast separation within the image by utilizing two scans at these different energy spectra. For example, a dual energy approach may facilitate an extraction of bone information or soft tissue information—or separate any two different arbitrary materials. There is also evidence that dual energy can improve coronary artery calcium detection, which is an indicator of cardiovascular disease. Note, however, that two images need to be generated (low energy and high energy), and there may be a delay between the two images due to the X-ray tube switching and detector read out time (e.g., a 150 ms delay). This could cause mis-registration between the two images because of patient/anatomy motion in that time period, which can cause blurring and/or artifacts in the final image.

Therefore, it would be desirable to design an apparatus and method to provide improved dual energy switching and energy capture.

BRIEF DESCRIPTION

According to some embodiments, an X-ray source is configured to generate X-rays directed toward an object, wherein the X-ray source is to: (i) generate a first energy X-ray pulse, (ii) switch to generate a second energy X-ray pulse, and (iii) switch back to generate another first energy X-ray pulse. A detector may be associated with multiple image pixels, and the detector includes, for each pixel: an X-ray sensitive element to receive X-rays; a first storage element and associated switch to capture information associated with the first energy X-ray pulses; and a second storage element and associated switch to capture information associated with the second energy X-ray pulse. A controller may synchronize the X-ray source and detector.

Some embodiments comprise: means for generating, by an X-ray source, a first energy X-ray pulse; means for switching the X-ray source to generate a second energy X-ray pulse; means for switching back the X-ray source to generate another first energy X-ray pulse, wherein a detector is associated with multiple image pixels and includes, for each pixel: an X-ray sensitive element to receive X-rays, a first storage element and associated switch to capture information associated with the first energy X-ray pulses, and a second storage element and associated switch to capture information associated with the second energy X-ray pulse; and means for synchronizing the X-ray source and detector by a controller.

A technical effect of some embodiments described herein may be an improved and accurate capturing of image information. Embodiments may be associated with systems and/or computer-readable medium storing instructions to perform any of the methods described herein.

FIGURES

Figure 2:
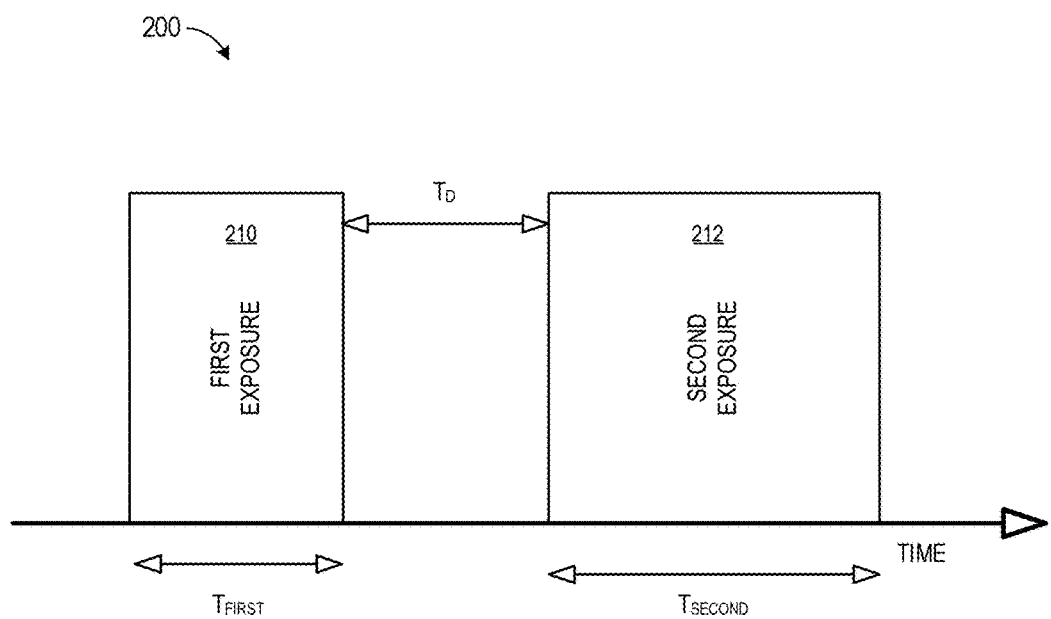
Figure 3:
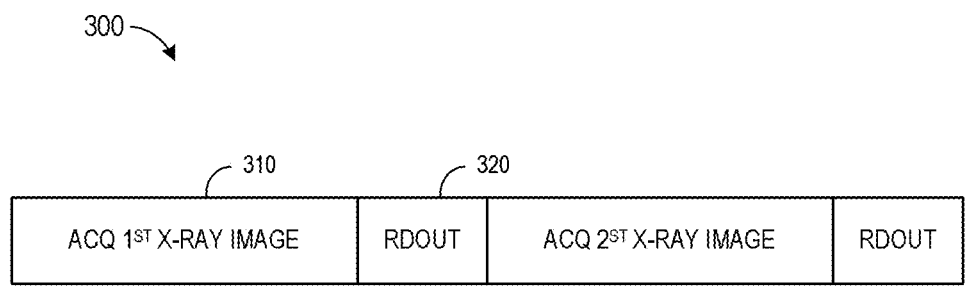
Figure 4:
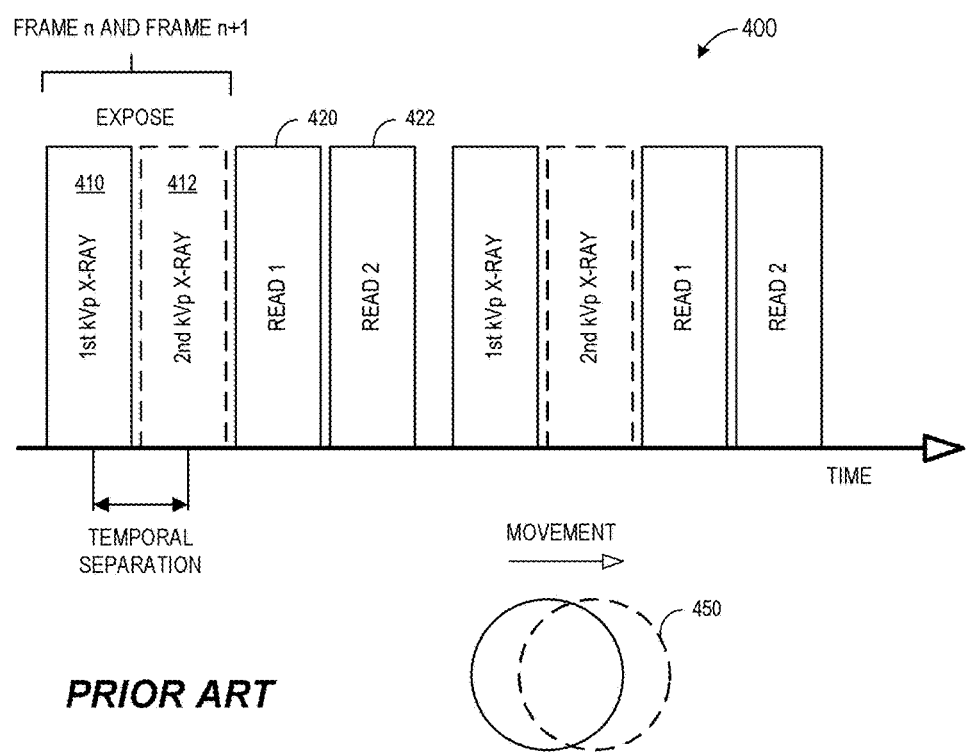
Figure 5:
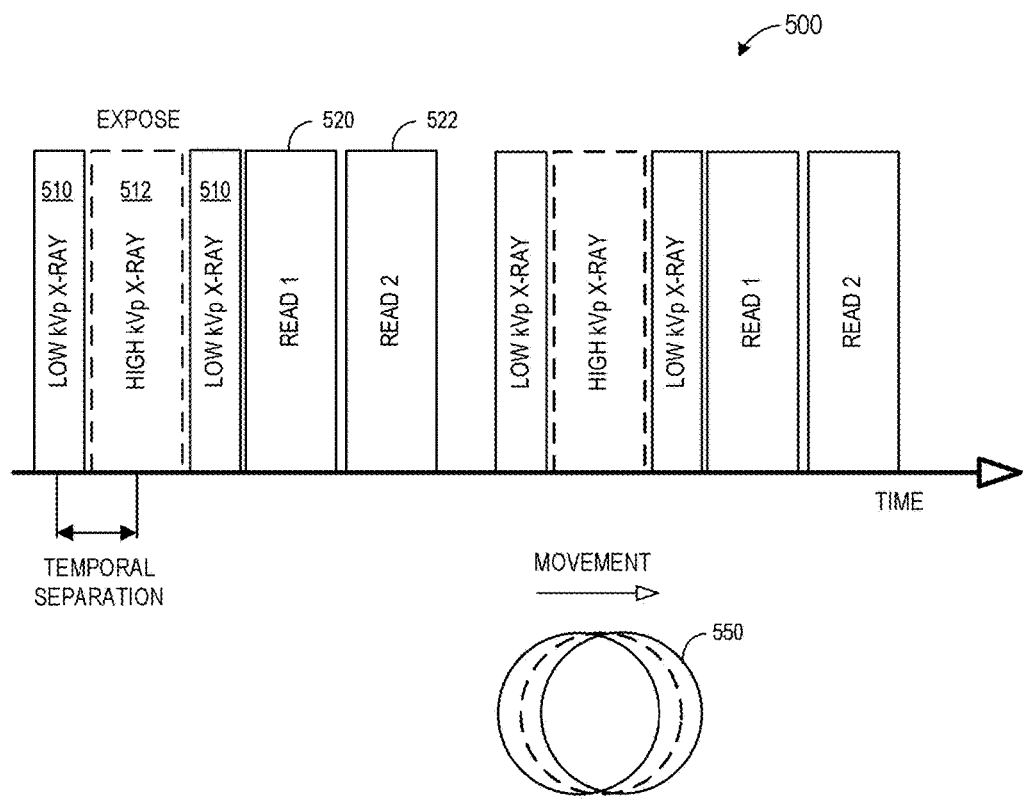
Figure 6:
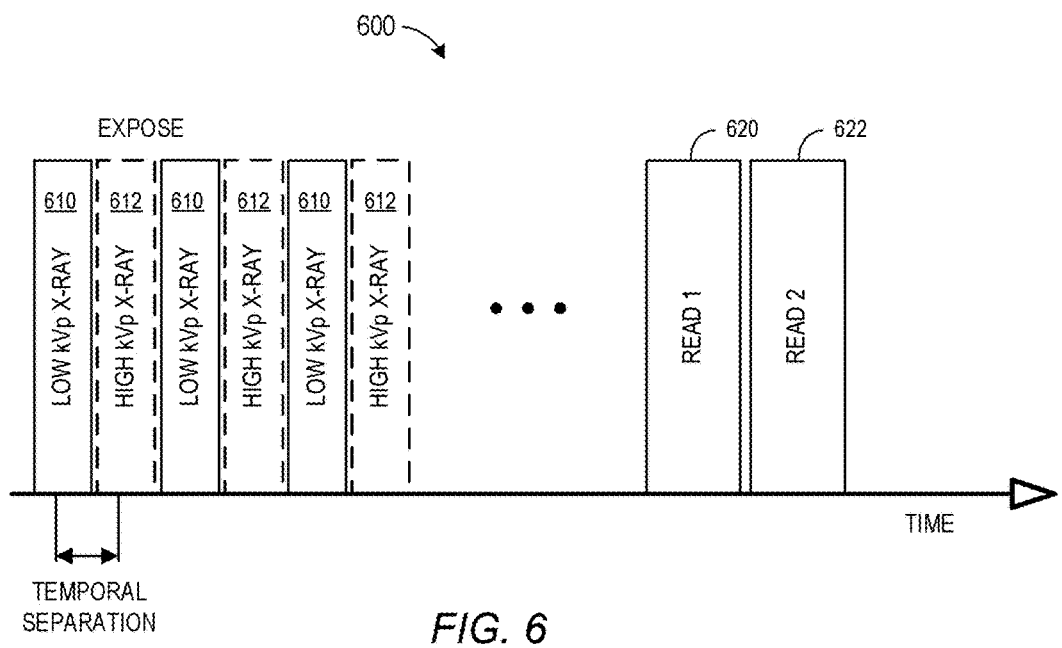
Figure 7:
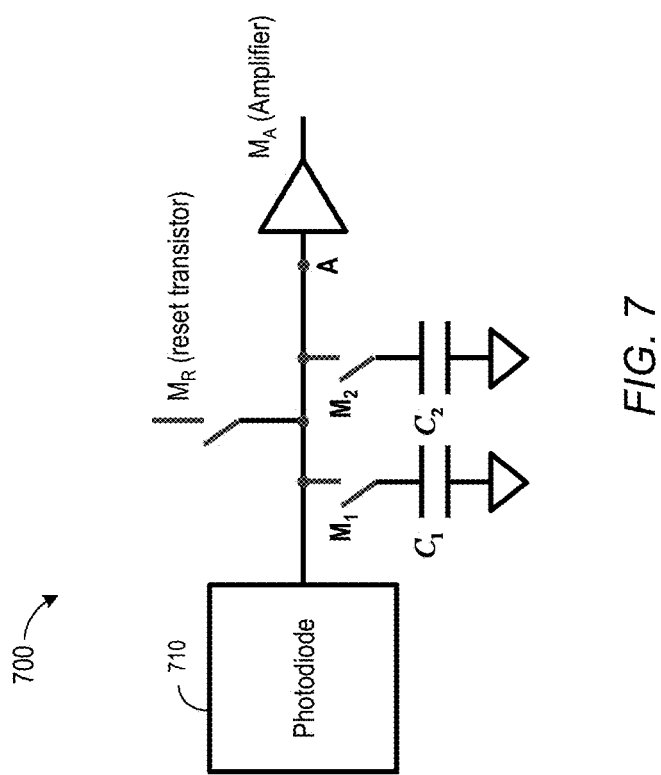
Figure 8:
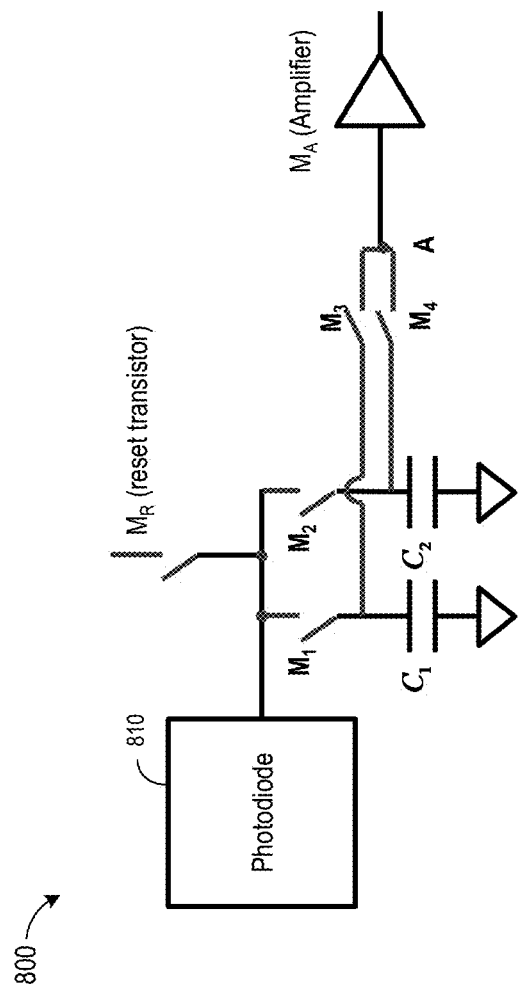
Figure 9:
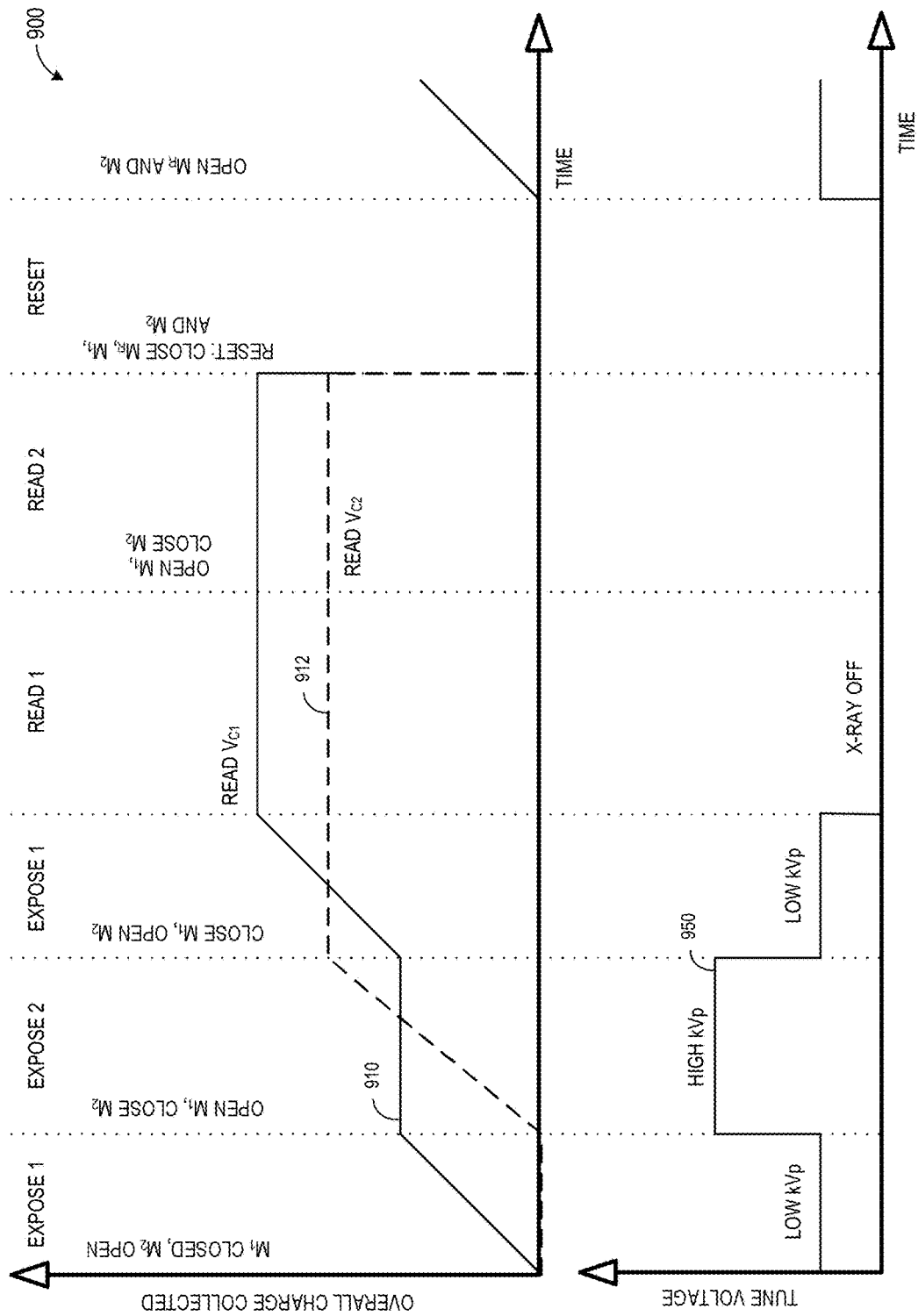
Figure 10:
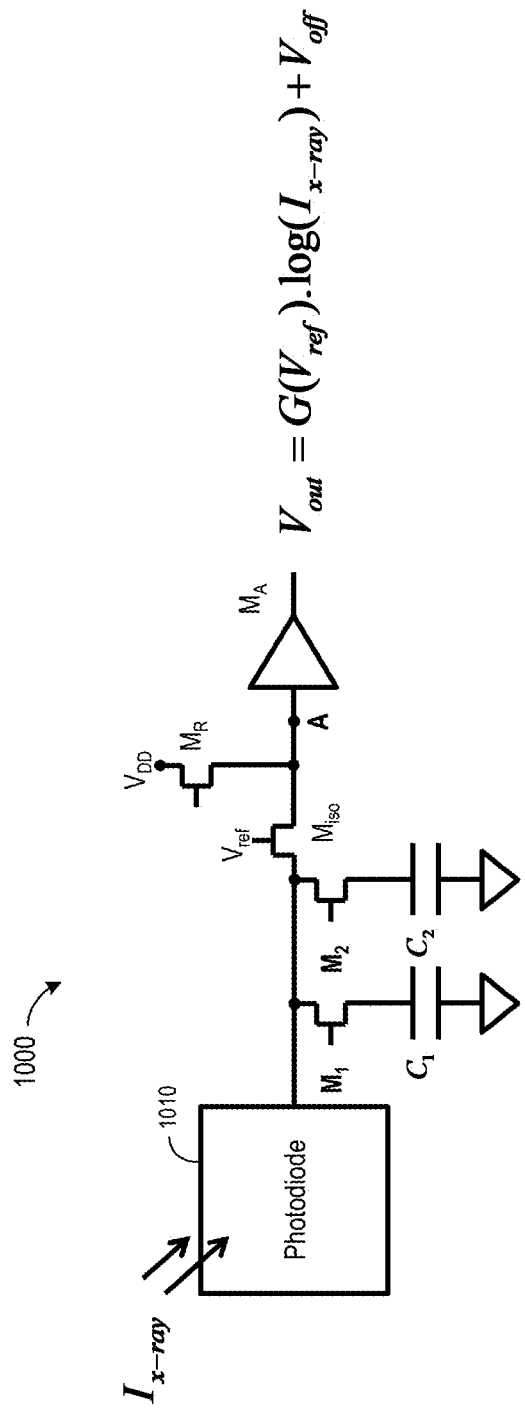
Figure 11:
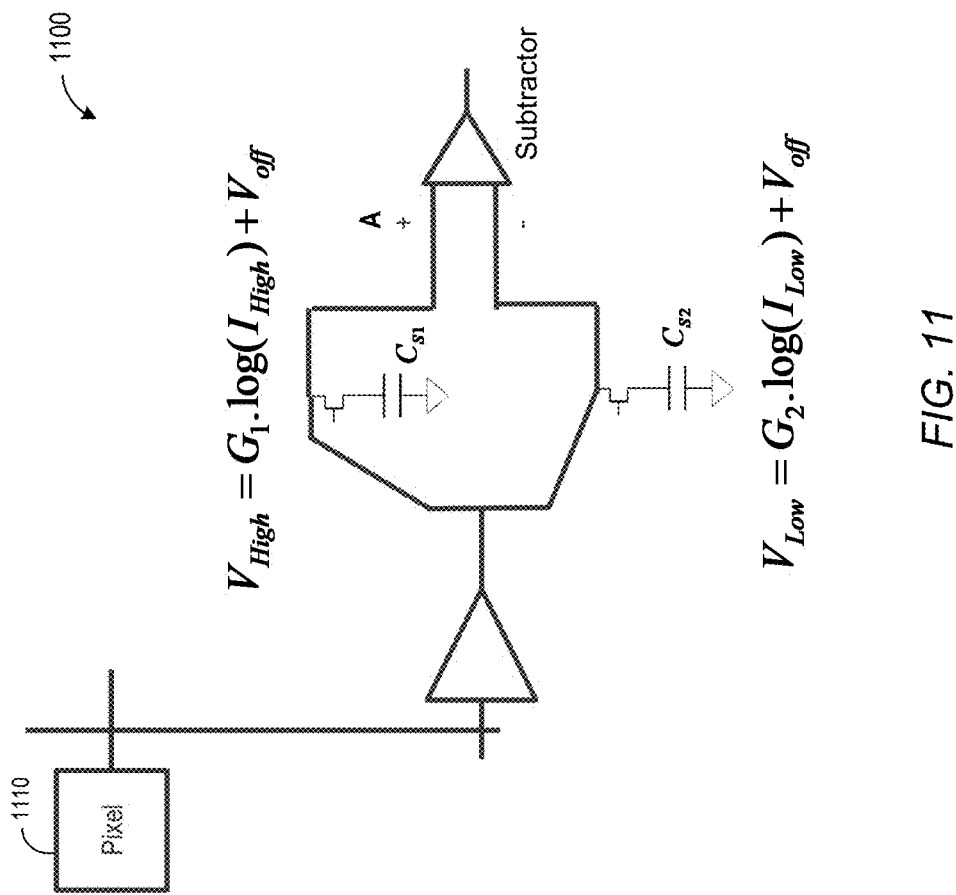
Figure 12:
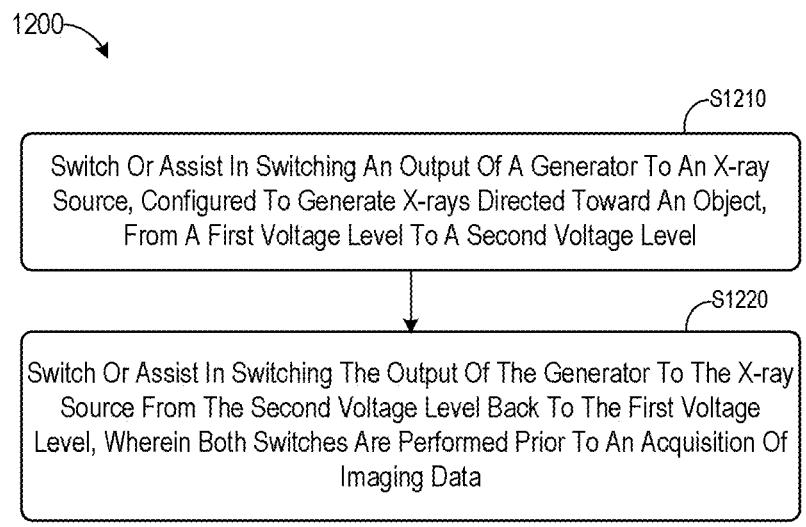
Figure 13:
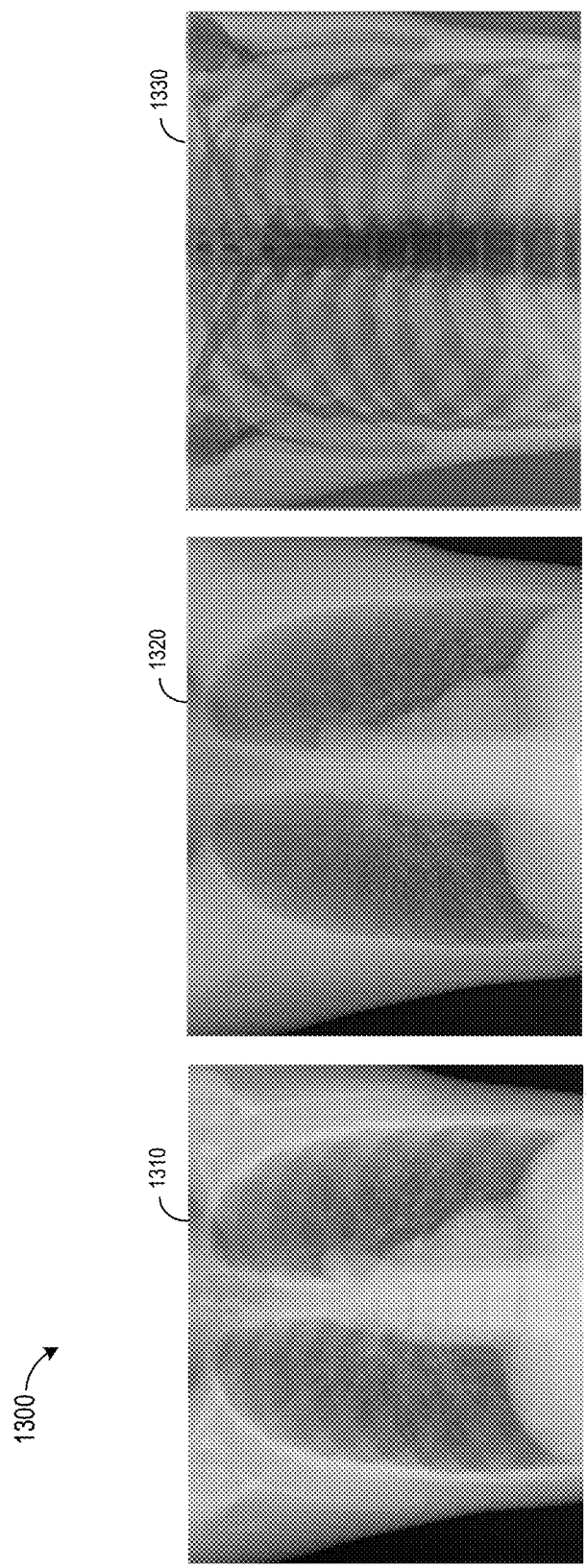

FIG. 1 illustrates a system using dual energy image acquisition in accordance with some embodiments.
FIG. 2 illustrates two exposures of energy.
FIG. 3 illustrates detector timing.
FIG. 4 illustrates dual energy pulses.
FIG. 5 is an example of dual energy pulses in accordance with some embodiments described herein.
FIG. 6 illustrates dual energy pulses according to some embodiments described herein.
FIG. 7 is a detector pixel schematic diagram of a dual well pixel in accordance with some embodiments.
FIG. 8 is a detector pixel schematic diagram of a dual well pixel having readout mode operation in accordance with some embodiments.
FIG. 9 illustrates a timing diagram according to some embodiments.
FIG. 10 is a detector pixel schematic diagram of a logarithmic pixel in accordance with some embodiments.
FIG. 11 is a detector pixel schematic diagram of a subtraction circuit in accordance with some embodiments.
FIG. 12 is a flow chart of a method associated with some embodiments.
FIG. 13 is an example of results that may be achieved according to some embodiments described herein.

DETAILED DESCRIPTION

FIG. 1 illustrates a system 100 using dual energy image acquisition in accordance with some embodiments. The system 100 comprises a patient 105 and a dual energy medical imaging system 110. The dual energy medical imaging system 110 comprises a detector 120, a user interface 130, an X-ray source 112, an image processing module 140, and a control module 160. In some embodiments, the dual energy medical imaging system 110 may be adjusted quickly for changes in imaging techniques.

The detector 120 converts X-rays to digital signals. The detector 120 may be, for example, a solid state detector. The detector 120 may adjust its operation relatively quickly (e.g., within 1 second). The dual energy medical imaging system 110 employs the detector 120 to produce an image based on energy, such as X-ray energy, transmitted through the patient 105.

The user interface 130 allows a user to input configuration information. The configuration information may include information such as patient information, anatomy, view and other techniques, such as kV, mA and exposure time. The dual energy medical imaging system 110 may be configured based on the user input from the user interface 130.

The image processing module 140 receives an image of the patient 105 from the dual energy medical imaging system 110 with detector 120. The image processing module 140 may process the images taken with high and low energy and generate soft tissue and bone images. The image processing module 140 may also process the soft tissue image and bone image and convert them into a final format presentable to a physician.

Note that the detector 120 may detect two different exposures of energy (e.g., a low energy pulse and a high energy pulse) generated by the X-ray source 112. FIG. 2 illustrates 200 two exposures of energy 210, 212. Further note that that with an improve speed of a detector in accordance with some embodiments described herein, the X-ray source 112 may need to be improved too to minimize the total scan time for DE.

As shown in FIG. 2, an overall time for a scan may include: $T_{FIRST}+T_D+T_{SECOND}$. Typically, $T_D$ is relatively long, such as around 140 ms, due to relatively slow detector read out time. $T_{FIRST}$ and $T_{SECOND}$ are exposure times and are relatively short as compared to $T_D$, such as from approximately 10 ms for 120 kVp and approximately 40 ms for 60 kVp (note that these examples may be associated with a chest X-ray image, and values associated with an abdomen X-ray image may be significantly longer). At 60 kVp, the required mAs may much bigger as compared to 120 kVp, such as approximately 5 to 10×. But because $T_D$ is long, a tube filament temperature may be increased to keep mA at 60 kVp similar to the mA at 120 kVp. The filament temperature can be changed in around 100 ms in a typical X-ray tube. Thus, a total DE scan time for a chest X-ray image using a typical system may be associated with: at 120 kV: 2 mAs, 200 mA, 10 ms, at 60 kV: 8 mAs, 200 mA, 40 ms, $T_D$=140 ms. $T_{TOTAL}$=40 ms+140 ms+10 ms=190 ms. Note that the tube mA at 60 kVp is almost the same as at 120 kV because the tube filament temperature may be changed within approximately 140 ms.

Now, with a new faster detector in accordance with some embodiments described herein, $T_D$ may be significantly reduced, such as from 140 ms to couple of ms. But now the tube may be too slow to change the filament temperature within couple of ms. As a result, mA at 60 kVp will drop, which will increase the exposure time at 60 kVp. This may offset some of the benefits gained from a fast detector.

To avoid such a result, in some embodiments no filament temperature change may be performed or the change may be performed slowly (not stabilized). For example, at 60 kVp, the tube may drop from 120 kVp's mA. This drop could be, for example, from approximately 10% to approximately 50%, depending on the tube current. Assuming that the tube current drops by 20%, a drop from 200 mA to 160 mA, then for low kVp, the exposure time will increase. The overall time may still be shorter than a traditional slow detector. For a chest X-ray image, for example, the over time is still much improved. For example, assume at 120 kV: 2 mAs, 200 mA, 10 ms, at 60 kV: 8 mAs, 150 mA, 53 ms, $T_D$ is 5 ms, so the total time is 10 ms+5 ms+53 ms=68 ms, which is still reduced significantly as compared to around 190 ms with a typical imaging system.

Another way of avoiding such a result may be to reduce the exposure time at 60 kVp, further by introducing a tube with an independently controlled mA. The mA can be controlled with a relatively short period of time, such as in the range of microseconds to milliseconds, independent of the kV. This may be, for example, a tube with specially designed electrodes or grids. The cathode may have an independent electrode to control the mA, so that mA is not affected by the tube kV. In some embodiments, at 60 kVp, the system may increase the mA more than at 120 kVp. For example, at 120 kV: 2 mAs, 200 mA, 10 ms, at 60 kV: 8 mAs, 400 mA, 20 ms. $T_D$ is still 5 ms, and now $T_{TOTAL}$=10 ms+20 ms+5 ms=35 ms, which is shorter than the 68 ms when no (or slow) filament temperature change was performed. Examples of a tube that may be associated with this approach are described, for example, in U.S. Pat. Nos. 8,320,521, 8,396,185, U.S. Pat. No. 8,027,433, and U.S. Pat. No. 8,401,151. Further note that this solution may have an even bigger benefit for abdomen X-ray images.

Referring now to FIG. 3, an example 300 of typical detector timing is illustrated. In particular a first X-ray image may be acquired 310 and then a readout operation 320 is performed to obtain image data. The process may then be repeated as needed. Note, however, that each readout operation 320 might take, for example 100 msec or more. As a result, patient movement during that time may cause the image data to be mis-registered causing artifacts and/or blurring in the ultimate diagnostic image.

FIG. 4 illustrates 400 dual energy pulses for Frame n and Frame n+1. In particular, a patient may be exposed to a 1st kVp energy pulse 410 (e.g., a low kVp energy pulse) followed by a 2nd kVp energy pulse 412 (e.g., a high kVp energy pulse). Note that there may (or may not) be a small delay between the different pulses 410, 412. After both exposures 410, 412, two separate readings 420, 422 may be taken (one for each energy level). Note that there still may be a temporal separation between the two exposures 410, 412. As a result, movement by the patient can still result in offset images 450.

According to some embodiments described herein, an ultra-fast DE may be achieved for general radiography. The delay between two exposures (high and low energy) may be, for example, in the range of several ms, resulting in reduced patient motion. This may be especially valuable, for example, with respect to a cardiac DE application, such as calcium detection in the coronary artery. Some embodiments may utilize a fast X-ray tube, a fast detector that can store two images at the pixel, and optionally, can produce a DE subtraction at the pixel level. According to some embodiments, the system may synchronize the tube X-ray emission and detector integration time. The delay between two exposures may be controlled at, for example, several ms. This may help reduce patient motion impact and improve image quality (e.g., the spatial resolution of the image). In the generator, the X-ray flux at the detector surface may or may not be substantially the same for both high kVp and low kVp exposures. Usually, the mAs at low kVp will be 3 to 10 higher than the high kVp mAs. For example, for a chest DE with medium size patient, high kVp is 120 kVp, 2 mAs, the low kVp is 60 kVp and 12 mAs. If using a tube current of 200 mA, then it may need 10 ms for high and 60 ms for low energy pulses. Sometimes, the low kVp may have less X-ray flux at the detector, and higher noise may result (e.g., quantum noise and electronic noise).

According to some embodiments, the X-ray tube and generator may generate two exposures at different kVp and mAs, typically from 50 kV to 140 kV. Moreover, the X-ray tube can switch the voltage from a high voltage generator directly from one kV to another. When the voltage is transitioning from low to high (or high to low), the electron beam emission may be suppressed by a bias voltage on the grid of the cathode. As a result, there may be no exposure during voltage transition. In the meantime, the filament temperature may need to change to emit high or low mA at different kVp, or the filament temperature may remain the same but the exposure time may be changed to adjust the mAs for different kVp. Such exposure time change might be controlled by turning on and off a main X-ray tube voltage or by a grid voltage close to the cathode. In another approach, the tube emission is not gridded off, and there may be a small amount of emission during the voltage transition (but the dose may be fairly small as compared to the main exposures). Note that a stable tube filament temperature may desirable to be stable during the second image. If not, it may desirable to control the exposure time to maintain the desired total mAs. The tube can transit from one voltage to another voltage in the range of several ms.

According to some embodiments, one of the two DE kVp pulses (e.g., the low kVp X-ray pulse) may be split into two pulses. The ratio of two split pulses may be desirable to be 50% each, but it can also be other percentages. In general, because low kVp pulses have longer exposure times, it may be desirable to split the low kVp pulse into two pulses. However, it is also possible to split the high kVp pulse. For example, FIG. 5 is an example 500 of DE pulses in accordance with some embodiments described herein. In particular, half of a low kVp X-ray pulse 510 is generated, followed by a full high kVp X-ray pulse 512, which is then followed by another half of the low kVp X-ray pulse 510. Moreover all of the switching may be performed before any image data is readout 520, 522. As a result, temporal separation may be reduced as compared to FIG. 4 (and the offset images 550 caused by movement by the patient can may be reduced). In such embodiments, the detector element may have two storage elements C1 and C2 as illustrated in FIG. 7. When the first pulse 510 may only turn on half of the time, and a M1 switch may be closed (allowing storage element C1 to collect low energy image data) while a M2 switch is open (preventing storage element C2 from collecting data). The system may then turn on the second kVp exposure for the full pulse width 512 with the M1 switch open (preventing storage element C1 from collecting data) while the M2 switch is closed (allowing storage element C2 to collect high energy image data). During the third pulse corresponding to the first kVp exposure 510, the M1 switch will again be closed while the M2 switch is open. The advantage is that it will reduce mis-registration due to any patient movement between exposures.

Another embodiment is to spit the two kVp image into many multiple small pules interleaved and arranged such that a mis-registration between high and low kVp may be reduced. Each small pulse might be, for example, in the range of several μs to several ms. FIG. 6 illustrates 600 dual energy pulses according to some embodiments described herein. To reduce movement artifacts between the low kVp pulses 610 and high kVp pulses 612 (e.g., to reduce temporal separation), it may be advantageous to split up both of the pulses 610, 612 into a plurality of smaller pulses prior to performing the reads 620, 622 for each energy level. The signal from each energy is stored into C1 and C2 storage element correspondingly. Because each pulse is very short, it may require that the X-ray tube kV be switched relatively quickly, and the detector M1 and M2 switches may also need to be fast.

FIG. 7 is a detector pixel schematic diagram of a dual well pixel 700 in accordance with some embodiments. The pixel 700 includes a photodiode 710 and two storage elements: (1) capacitor C1 and associated switch M1, and (2) capacitor C2 and associated switch M2. C1 and M1 might be associated with, for example, low energy X-ray while C2 and M2 are associated with high energy X-ray. The photodiode 710 may, for example, be implemented as a pinned photodiode with a substantially lower capacitance as compared to C1 or C2 to enable fast and nearly complete charge transfer to the storage capacitances, C1 and C2. Note that the capacitances C1 and C2 may be designed to meet dynamic range requirements of the low kVp and high kVp X-ray pulses. Moreover, the switches M1 and M2 may enable relatively fast (e.g., less than 1 μs) and efficient charge separation between the low kVp and high kVp X-ray pulses.

According to some embodiments, the pixel 700 further includes an in-pixel amplifier $M_A$ to enable low electronic noise and to reduce readout time. According to some embodiments, the pixel 700 further may include multiple capacitors and associated switches (e.g., an array or set of 100 or more capacitors and switches). This in-pixel storage can enable multi-projection imaging applications like tomography, or fluorography, and/or image paste applications. For example, for a fast tomosynthesis dual energy application, there could be 20 images, including 10 low energy images and 10 high energy images. For a fast tomosynthesis single energy application, there might be 20 images with the same X-ray energy. During the tomosynthesis scan, each image intensity is stored in a corresponding capacitor (C1 . . . C200). After the tomosynthesis scan is complete, all 200 images stored on each capacitor will be read out accordingly. Note that such a pixel 700 may also support wireless detectors (e.g., by storing the images locally to be readout later). A reset transistor $M_R$ may be used to reset the pixel 700 after image data readout is performed from C1 and C2.

Thus, according to some embodiments, the detector or pixel 700 may comprise a digital detector and each pixel 700 has a photodiode 710, storage capacitors, and a transistor to facilitate readout. At each pixel 700, there may be two storage capacitors (C1 to store the image information from one kVp and C2 to store the image information from another kVp). One embodiment is that each capacitor has a switch (M1 and M2) to control the signal flow. For example, when one kVp X-ray is on, C1 switch M1 is closed and C2 switch C2 is open (and only C1 is charged). When the second kVp exposure is on, C1 switch M1 is open and C2 switch M2 is closed (and only C2 is charged). When it is time to readout data, each switch can be used similarly to read out the signals from C1 and C2.

In some embodiments, the X-ray flux and therefore the signals from high kV and low kV exposure are substantially different. In order to balance the electronic signal, each C1 and C2 value can be dynamically changed, according to some embodiments, based on the imaging protocols. The change of capacitor might be, for example, either by dynamically grouping multiple capacitors together or by changing the electrical property of each individual capacitor. The optimization may help ensure that the voltage on C1 and C2 are comparable for both high kVp and low kVp signals.

In another embodiment, there is only one switch on one capacitor (e.g., C1) and no switch on C2. When the first kVp exposure is performed, the C1 switch is closed, so that both capacitors are charged. The ratio of the charge in each capacitor may be linearly proportional to the capacitance (and this ratio is known). Before the second kVp exposure is performed, the C2 capacitor is reset to zero. When the second kVp exposure is performed, the C1 switch is open and the signal is only integrated on C2. During or after readout, (because a known certain percentage of the signal of the first exposure is lost), the system may scale that signal back according to the capacitor ratio C2/C1. The C2 signal is already correct. By doing this, one less switch may be used. According to some embodiments, C2 capacitance may be substantially smaller as compared to C1 capacitance (e.g., using different capacitors for different kVp). The system might, for example, use C1 for high kVp signal and C2 for low kVp signal. By doing that, comparable voltage levels from the two capacitors may be maintained.

In addition to what is described in FIG. 7, a readout mode structure can be implemented to enable fast readout of one capacitor, while the other capacitor charges, with the addition of M3 and M4 switches. FIG. 8 is a detector pixel schematic diagram of a dual well pixel 800 having readout mode operation in accordance with some embodiments. As before, the pixel 800 includes a photodiode 810 and two storage elements: (1) capacitor C1 and associated switch M1, and (2) capacitor C2 and associated switch M2. The pixel 800 further includes an in-pixel amplifier $M_A$ to enable low electronic noise and to reduce readout time. A reset transistor $M_R$ may be used to reset the pixel 800 after image data readout is performed from C1 and C2. According to this embodiment, the M3 and M4 switches may be timed the same as M2 and M1, respectively. With readout mode operation, and fast readout electronics, the dual-well pixel 800 may be operated in various combinations of split pulses. That is, the readout mode operation can help eliminate the leakage issue when a charge signal is stored on a pixel capacitor (when a CMOS capacitor typically exhibits limited resistance to ground).

FIG. 9 illustrates a timing diagram 900 according to some embodiments. In particular, the top graph illustrates an overall charge collected for a low voltage pulse 910 and a high voltage pulse 912 over time. Moreover, the bottom graph indicates the voltage level 950 of the X-ray source over the same period of time. As can be seen, when M1 is closed and M2 is open, the low kVp energy is collected in C1 during exposure 1. M1 is then opened and M2 is closed so that high kVp energy can be collected in C2 during exposure 2. M1 is then closed and M2 is opened so that the remaining low kVp energy is again collected in C1 during exposure 3. Information may be read from C1 and C2 and the pixel may be reset before the next series of pulses are transmitted.

FIG. 10 is a detector pixel schematic diagram of a logarithmic pixel 1000 in accordance with some embodiments. By adding one more transistor $M_{iso}$, the pixel 1000 output can be made respond to the logarithm of the photo charge collected at a photodiode 1010 (as compared to the linear output resulting from the circuits of FIGS. 7 and 8). In particular, the output may be represented as:

$$V_{out} = G(V_{ref}) \cdot \log(I_{x-ray}) + V_{off}$$

The operation of the pixel 1000 to achieve logarithmic repose is described, for example, in IEEE TRANSACTIONS ON ELECTRON DEVICES, Vol. 56, No. 11, November (2009). This at-pixel 1000 logarithmic operation can be helpful, for example, to avoid needing to perform such an operation later in a software application. Note that the $V_{ref}$ and the gain G may be used to control responsivity of the pixel 1000. Thus, the capacitor voltage value is no longer proportional to the integrated X-ray signal, but instead to the logarithm of the X-ray signal. This is achieved by close the transistor $M_{iso}$ during the integration.

Similarly, a circuit may perform a subtraction operation to likewise avoid needing to perform such an operation later in a software application (improving the speed of the software application). FIG. 11 is a detector pixel schematic diagram of a subtraction circuit 1100 in accordance with some embodiments. In this example, a bone image may be constructed from pixel 1110 data by subtracting a weighted log(low kVp image) from log(high kVp image). This might be implemented, for example, a the pixel 1100 as follows:

Integrate High kVp and sample the log response on pixel capacitance, C1;
Integrate Low kVp and sample the log response on pixel capacitance, C2;
Read High kVp pixel value and store it on column capacitor, CS1;
Read Low kVp pixel value and store it on column capacitor, CS2; and
Subtract the sample voltage CS2 from CS1 to obtain the resulting bone image.

This can be repeated for soft tissue with a different set of gain:

$$Bone = \ln(I_{High-kVp}) - w_B \cdot \ln(I_{Low-kVp})$$

$$Soft = \ln(I_{High-kVp}) - w_S \cdot \ln(I_{Low-kVp})$$

Note that CS1 might be associated with $V_{High} = G_1 \cdot \log(I_{High}) + V_{off}$ and CS2 might be associated with $V_{Low} = G_2 \cdot \log(I_{Low}) + V_{off\_low}$. The circuit 1100 may be associated with a pixel of a column of image information. For example, information may be simultaneously captured and, subsequently, simultaneously read out, for a plurality of pixels within an image column. During the readout, both logarithms of the signal are read out by column read out circuits. Each column read out circuit has two subtraction circuits. One input is from the C1 voltage with an amplification factor, and the other input is from the C2 voltage with another amplification factor, and the output is the subtracted image. By carefully choosing the amplification factors, the image can be tuned to represent a bone image. In a simple case, only one amplifier might be used (not two). Similarly for the second subtraction circuit, the amplification for each C1 and C2 may be chosen such that the output is a soft tissue image. In another embodiment, there is only one subtraction circuit, which is first used to process a bone image and then process the soft tissue image. The amplification factor may be dynamically changed, according to some embodiments, with inputs being based on patient information and protocols.

FIG. 12 is a flow chart of a method 1200 in accordance with some embodiments. The flow charts described herein do not imply a fixed order to the steps, and embodiments of the present invention may be practiced in any order that is practicable. Note that any of the methods described herein may be performed by hardware, software, or any combination of these approaches. For example, a computer-readable storage medium may store thereon instructions that when executed by a machine result in performance according to any of the embodiments described herein.

At S1210, the system may switch an output of a generator to an X-ray source, configured to generate X-rays directed toward an object, from a first voltage level to a second voltage level. Note that the system may directly switch the output of the generator to the X-ray source or "assist in switching" the energy level. As used herein, the phrase "assist in switching" includes situations where the energy level is changed at the generator, at a switching unit, within the X-ray source, and/or by any other means.

At S1220, the system may switch (or assisting in switching) the output of the generator to the X-ray source from the second voltage level back to the first voltage level, wherein both switches are performed prior to an acquisition of imaging data. Note that X-rays having a first energy spectrum may be generated by the X-ray source when the first voltage level is applied and X-rays having a second energy spectrum may be generated by the X-ray source when the second voltage level is applied.

After the exposures of S1210 and S1220, a computer system may acquire imaging data from X-rays generated at the first and second voltage levels and reconstruct at least one image from the imaging data. According to some embodiments, the second voltage level is higher than the first voltage level. The imaging data may be captured and/or collected, according to some embodiments, via a dual well pixel that includes: (i) an X-ray sensitive element (such as a photodiode) to receive X-rays, (ii) a first storage element and associated switch to capture information associated with the first voltage level, and (iii) a second storage element and associated switch to capture information associated with the second voltage level. The first and second storage elements might comprise, for example, Complementary Metal-Oxide Semiconductor ("CMOS) capacitors C1 and C2. Moreover, the photodiode may comprise a pinned photodiode with substantially lower capacitance as compared to C1 or C2 to enable complete charge transfer to C1 and C2. The capacitances of C1 and C2 may be selected based on dynamic range requirements of low energy and high energy X-ray pulses. According to some embodiments, the pixel further includes: a reset switch connecting an output of the pixel to a known reset voltage, and an amplifier with an output connected to the output of the pixel to facilitate a substantially low electronic noise and substantially fast readout from the pixel. Moreover, as described with respect to FIG. 8, the dual well pixel might have readout mode operation such that C1 charges while C2 is read and C2 charges while C1 is read, and further includes: a first switch coupled between C1 and the output amplifier, and a second switch coupled between C2 and the output amplifier.

As described with respect to FIG. 10, the dual well pixel might further includes a transistor such that the output of the pixel responses logarithmically to a photo-charge of the photodiode. As described with respect to FIG. 11, the dual well pixel may further include a subtraction element such that the output of the pixel is associated with a difference between a charge stored in C1 and a charge stored in C2. Moreover, a weighting factor is applied to at least one of a charge stored in C1 and a charge stored in C2, and at least one weighting factor may be selected based on at least one of bone density and soft tissue density. According to some embodiments, a reference voltage may be used to control the gain of the logarithmic amplifier resulting in the weighting factor. For example, FIG. 13 is an illustration of results 1300 that may be achieved according to some embodiments described herein. In particular, the results 1300 include a first image 1310 with normal tuning, a second image 1320 with tuning tailored for soft tissue, and a third image 1330 with tuning tailored for bone.

Thus some embodiments may reduce delay time to several ms, which may significantly reduce the mis-registration. Another aspect to reduce the patient motion is that embodiments may reduce the exposure time for low kVp exposures, because this is the longest time to contribute to the overall time. By choosing an optimized capacitance value to match the dose, noise can be reduced. Although some embodiments have been described with respect to X-ray data, note that embodiments might be practiced in connection with tomosynthesis scan data, fluorography data, image paste data, and/or wireless detectors. Note that DE fluorography may have multiple exposures during the scan. Doing DE on fluorography may be difficult because it takes a long time to process the DE subtraction by software. By doing DE processing on detector, embodiments may significantly reduce the time it takes to generate bone or soft tissue images. Still further, doing DE subtraction at detector may further simplify the system design.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

For example, although many embodiments have been described with respect to DE systems, note that embodiments may be used in connection with a single energy tomosynthesis imaging system. For example, the system may include a gantry having an opening for receiving an object to be scanned, and an X-ray source configured to generate X-rays directed toward the object. During the scan, X-ray source will move from starting location to end location, via a predefined trajectory. The detector may or may not move during the scan. The system may further include a set of dual well pixels, each pixel including: (1) a photodiode to receive X-rays, (2) a plurality of n storage elements and associated switches to capture information associated with the X-rays, wherein the storage elements comprise capacitors C1 through Cn; and (3) a computer to acquire imaging data from the set of dual well pixels and to reconstruct at least one image from the imaging data. Such an arrangement might be helpful, for example, when the X-ray source is a single energy X-ray source or DE X-ray source. In either case, n might comprise, for example, an integer value from 10 to 100.

As another example, embodiments described herein may be used to dynamically tune C1 and/or C2 in a pixel. Consider, for example, a system including an X-ray source configured to generate X-rays directed toward an object, including a first pulse of X-rays having a first energy spectrum and a second pulse of X-rays having a second energy spectrum. Moreover, the system further includes a dual well pixel, including: (1) an x-ray sensitive element to receive X-rays, (2) a first storage element and associated switch to capture information associated with the first energy spectrum, and (3) a second storage element and associated switch to capture information associated with the second energy spectrum, wherein the first and second storage elements comprise capacitors C1 and C2, and the capacitance of C1 and C2 are selected based at least in part on the first and second energy spectrums. This could be achieved, for example, using a bank of capacitors $C_1$ through $C_n$, where at least one subset of the bank of capacitors is dynamically selected to create at least one of C1 and C2.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A system, comprising:
an X-ray source configured to generate X-rays directed toward an object, wherein the X-ray source is to: (i) generate a first energy X-ray pulse, (ii) switch to generate a second energy X-ray pulse, and (iii) switch back to generate another first energy X-ray pulse, wherein the second energy X-ray pulse is associated with higher voltage level as compared to the first energy X-ray pulses;
a detector associated with multiple image pixels, the detector including, for each pixel:
an X-ray sensitive element to receive X-rays,
a first storage element and associated switch to capture information associated with the first energy X-ray pulses, and
a second storage element and associated switch to capture information associated with the second energy X-ray pulse; and
a controller to synchronize the X-ray source and detector.

2. The system of claim 1, further comprising a computer configured to:
   acquire imaging data associated with the first and second energy X-ray pulses; and
   reconstruct at least one image from the imaging data.

3. The system of claim 1, wherein the first and second storage elements comprise capacitors C1 and C2.

4. The system of claim 3, wherein the X-ray sensitive element comprises a photodiode with a capacitance significantly lower than capacitance of C1 and C2 to enable fast and substantially complete charge transfer to C1 and C2.

5. The system of claim 3, wherein the X-ray sensitive element is a pinned photodiode.

6. The system of claim 3, wherein the capacitances of C1 and C2 are selected based on dynamic range requirements of low energy and high energy X-ray pulses.

7. The system of claim 3, wherein one end of C1 and C2 are connected to a common reference voltage, the other end of C1 and C2 are connected through a first switch and a second switch to an output of the pixel, and for each pixel the detector further includes:
   a reset switch connecting the output of the pixel to a known reset voltage,
   an amplifier with an input connected to the output of the pixel to facilitate a substantially low electronic noise and substantially fast readout from the pixel,
   a first switch coupled between C1 and the output of the pixel, and
   a second switch coupled between C2 and the output of the pixel.

8. The system of claim 3, wherein the detector has readout mode operation such that C1 charges while C2 is read and C2 charges while C1 is read, and further includes for each pixel:
   a first switch connecting C1 to an output of the pixel,
   a second switch connecting C2 to the output of the pixel,
   a third switch connecting C1 to the input of the amplifier, and
   a fourth switch connecting C2 to the input of the amplifier.

9. The system of claim 3, wherein for each pixel the detector further includes:
   a transistor such that the output of the pixel responses logarithmically to a photo-charge of the photodiode, wherein a reference voltage is used to control the gain of a logarithmic amplifier resulting in a weighting factor.

10. The system of claim 9, wherein at least one weighting factor is selected based on at least one of bone density and soft tissue density.

11. The system of claim 3, wherein for each column the detector further includes:
   a subtraction element such that the output of the pixel is associated with a difference between a charge stored in C1 and a charge stored in C2.

12. The system of claim 3, wherein a weighting factor is applied to at least one of a charge stored in C1 and a charge stored in C2.

13. A method, comprising:
   generating, by an X-ray source, a first energy X-ray pulse;
   switching the X-ray source to generate a second energy X-ray pulse;
   switching back the X-ray source to generate another first energy X-ray pulse, wherein the second energy X-ray pulse is associated with higher voltage level as compared to the first energy X-ray pulses, and
   wherein a detector is associated with multiple image pixels and includes, for each pixel: an X-ray sensitive element to receive X-rays, a first storage element and associated switch to capture information associated with the first energy X-ray pulses, and a second storage element and associated switch to capture information associated with the second energy X-ray pulse; and
   synchronizing the X-ray source and detector by a controller.

14. The method of claim 13, further comprising:
   acquiring imaging data associated with the first and second energy X-ray pulses; and
   reconstructing at least one image from the imaging data.

15. The method of claim 13, wherein the first and second storage elements comprise capacitors C1 and C2.

16. The method of claim 15, wherein the photodiode comprises a pinned photodiode with capacitance significantly lower than capacitance of C1 and C2 to enable complete charge transfer to C1 and C2, and the capacitances of C1 and C2 are selected based on dynamic range requirements of low energy and high energy X-ray pulses.

* * * * *